US005739029A

United States Patent [19]

King et al.

[11] Patent Number: 5,739,029
[45] Date of Patent: Apr. 14, 1998

[54] VECTORS FOR EXPRESSION OF G PROTEIN COUPLED RECEPTORS IN YEAST

[75] Inventors: Klim King, Durham, N.C.; Henrik G. Dohlman, Berkeley, Calif.; Marc G. Caron; Robert J. Lefkowitz, both of Durham, N.C.

[73] Assignee: Duke University, Durham, N.C.

[21] Appl. No.: 441,291

[22] Filed: May 15, 1995

Related U.S. Application Data

[62] Division of Ser. No. 71,355, Jun. 3, 1993, Pat. No. 5,482,835, which is a continuation of Ser. No. 581,714, Sep. 13, 1990, abandoned.

[51] Int. Cl.$^6$ .............................. C12N 1/19; C12N 15/62; C12N 15/81
[52] U.S. Cl. ..................... 435/254.21; 435/69.1; 435/69.7; 435/252.3; 435/320.1; 435/7.1; 435/7.2; 536/23.5
[58] Field of Search ................ 435/69.1, 69.7, 435/7.1, 22, 252.3, 320.1, 254.27; 536/23.5

[56] References Cited

U.S. PATENT DOCUMENTS

| | | | |
|---|---|---|---|
| 4,546,082 | 10/1985 | Kurjan et al. | 435/172.3 |
| 4,615,974 | 10/1986 | Kingsman et al. | 435/68 |
| 4,775,622 | 10/1988 | Hitzeman et al. | 435/68 |
| 4,797,359 | 1/1989 | Finkelstein | 435/68 |
| 4,865,989 | 9/1989 | Hitzeman et al. | 435/320 |
| 4,876,197 | 10/1989 | Burke et al. | 435/172.3 |
| 4,880,734 | 11/1989 | Burke et al. | 435/68 |
| 5,215,915 | 6/1993 | Tiberi et al. | 435/252.3 |
| 5,242,822 | 9/1993 | Marullo et al. | 435/252.3 |
| 5,245,011 | 9/1993 | Tiberi et al. | 530/350 |
| 5,310,662 | 5/1994 | Evans et al. | 435/64.1 |
| 5,352,660 | 10/1994 | Pawson | 514/12 |
| 5,364,791 | 11/1994 | Vegeto et al. | 435/320.1 |
| 5,384,243 | 1/1995 | Gutkind et al. | 435/6 |
| 5,389,543 | 2/1995 | Bunzow et al. | 435/252.3 |
| 5,401,629 | 3/1995 | Harpold et al. | 435/6 |
| 5,436,128 | 7/1995 | Harpold et al. | 435/6 |
| 5,468,615 | 11/1995 | Chio et al. | 435/7.2 |
| 5,482,835 | 1/1996 | King et al. | 435/6 |

FOREIGN PATENT DOCUMENTS

| | | |
|---|---|---|
| 0 123 544 | 10/1984 | European Pat. Off. . |
| WO 90/05780 | 5/1990 | WIPO . |
| WO 91/12273 | 8/1991 | WIPO . |
| WO 91/15583 | 10/1991 | WIPO . |
| WO 92/10583 | 6/1992 | WIPO . |
| WO 92/19723 | 11/1992 | WIPO . |

OTHER PUBLICATIONS

Dietzel et al. *Cell* 50:1001–1010, Sep. 25, 1987.
Bunzow, J. et al., "Cloning and Expression of a Rat $D_2$ Dopamine Receptor cDNA," *Nature*, vol. 336, 783–787 (1988).
Chen, Y. et al., "Shc Adaptor Proteins are Key Transducers of Mitogenic Signaling Mediated by the G Protein–coupled Thrombin Receptor," *The EMBO Journal*, vol. 15, No. 5, 1037–1044 (1996).

Coso, O. et al., "Signaling from G Protein–coupled Receptors to c–Jun Kinase Involves βγ Subunits of Heterotrimeric G Proteins Acting on a Ras and Rac1–dependent Pathway," *The Journal of Biological Chemistry*, vol. 271, No. 8, 3963–3966 (1996).
Dhanasekaran, N. et al., "G Protein–coupled Receptor Systems Involved in Cell Growth and Oncogenesis," *Endocrine Reviews*, vol. 16, No. 3, 259–270 (1995).
Dohlman, H. et al., "Inhibition of G–Protein Signaling by Dominant Gain–of–Function Mutations in Sst2p, a Pheromone Desensitization Factor in Saccharomyces ceravisiae," *Molecular and Cellular Biology*, vol. 15, No. 7, 3635–3643 (1995).
Fujita, N. e al., "Biosynthesis of the Torpedo californica Acetylcholine Receptor α Subunit in Yeast," *Science*, vol. 231, 1284–1287 (1986).
Huang, H. et al., "Functional Expression of Rat M5 Muscarinic Acetylcholine Receptor in Yeast," *Biochemical and Biophysical Research Communications*, vol. 182, No. 3, 1180–1186 (1992).
Kao, L. et al., "Interactions Between the Ankyrin Repeat–Containing Protein Akr1p and the Pheromone Response Pathyway in Saccharomyces cervisiae," *Molecular and Cellular Biology*, vol. 16, No. 1, 168–178 (1996).
King K. et al., "Control of Yeast Mating Signal Transduction by a Mammalian β$_2$–Adrenergic Receptor and G$_s$ α Subunit," *Science*, vol. 250, 121–123 (1990).
Kingsman, S.M. et al., "The Production of Mammalian Proteins in Saccharomyces cerevisiae," *TIBTECH*, vol. 5, 53–57 (1987).
Mahadevan, M. et al., "Short Communication: Isolation of a Novel G Protein–Coupled Receptor (GPR4) Localized to Chromosome 19q13.3," *Genomics*, vol. 30, 84–88 (1995).
Nagayama, Y. et al., "Involvement of G Protein–coupled Receptor Kinase 5 in Homologous Desensitization of the Thyrotropin Receptor," *The Journal of Biological Chemistry*, vol. 271, No. 17, 10143–10148 (1996).

(List continued on next page.)

*Primary Examiner*—John Ulm
*Attorney, Agent, or Firm*—Lahive & Cockfield, LLP; Giulio A. DeConti, Jr.; Catherine J. Kara

[57] ABSTRACT

Disclosed is a transformed yeast cell containing a first heterologous DNA sequence which codes for a mammalian G protein coupled receptor and a second heterologous DNA sequence which codes for a mammalian G protein α subunit (mammalian G$_α$). The first and second heterologous DNA sequences are capable of expression in the cell, but the cell is incapable of expressing an endogenous G protein α-subunit (yeast G$_α$). The cells are useful for screening compounds which affect the rate of dissociation of G$_α$ from G$_{βγ}$ in a cell. Also disclosed is a novel DNA expression vector useful for making cells as described above. The vector contains a first segment comprising at least a fragment of the extreme amino-terminal coding sequence of a yeast G protein coupled receptor. A second segment is positioned downstream from the first segment (and in correct reading frame therewith), with the second segment comprising a DNA sequence encoding a heterologous G protein coupled receptor.

12 Claims, 3 Drawing Sheets

OTHER PUBLICATIONS

Nomoto, S. et al., "Regulation of the Yeast Pheromone Response Pathway by G Protein Subunits," *The EMBO Journal*, vol. 9, No. 3, 691–696 (1990).

Payette, P. et al., "Expression and Pharmacological Characterization of the Human M1 Muscarinic Receptor in Saccharomyces cerevisiae," *FEBS*, vol. 266, No. 1,2 21–25 (1990).

Stevenson, B. et al., "Mutation of RGA1, which Encodes a Putative GTPase–activating Protein for the Polarity–establishment Protein Cdc42p, Activates the Pheromone–response Pathway in the Yeast Saccharomyces cerevisiae," *Genes & Development*, vol. 9, 2949–2963 (1995).

Stryer, L. "G Proteins: A Family of Signal Transducers," *Ann. Rev. Cell Biol.*, vol. 2, 391–419 (1986).

Trueheart, J. et al., "Two Genes Required for Cell Fusion During Yeast Conjugation: Evidence for a Pheromone–Induced Surface Protein," *Molecular and Cellular Biology*, vol. 7, No. 7, 2316–2328 (1987).

5,739,029

VECTORS FOR EXPRESSION OF G PROTEIN COUPLED RECEPTORS IN YEAST

This is a divisional of application Ser. No. 08/071,355, filed Jun. 3, 1993, now U.S. Pat. No. 5,482,835, which is a continuation of application Ser. No. 07/581,714, filed Sep. 13, 1990, now abandoned.

This invention was made with government support under NIH grants HL16037 and GM21841. The government may have certain rights to this invention.

FIELD OF THE INVENTION

This invention relates to yeast cells expressing heterologous G protein coupled receptors, vectors useful for making such cells, and methods of using the same.

BACKGROUND OF THE INVENTION

The actions of many extracellular signals (for example, neurotransmitters, hormones, odorants, light) are mediated by receptors with seven transmembrane domains (G protein coupled receptors) and heterotrimeric guanine nucleotide-binding regulatory proteins (G proteins). See H. Dohlman, M. Caron, and R. Lefkowitz, *Biochemistry* 26, 2657 (1987); L. Stryer and H. Bourne, *Ann. Rev. Cell Biol.* 2, 391 (1988). Such G protein-mediated signaling systems have been identified in organisms as divergent as yeast and man. See H. Dohlman et al., supra; L. Stryer and H. Bourne, supra; K. Blumer and J. Thorner, *Annu.Rev. Physiol.* (in press). The β2-adrenergic receptor (βAR) is the prototype of the seven-transmembrane-segment class of ligand binding receptors in mammalian cells. In response to epinephrine or norepinephrine, βAR activates a G protein, $G_s$, which in turn stimulates adenylate cyclase and cyclic adenosine monophosphate production in the cell. See H. Dohlman et al., supra; L. Stryer and H. Bourne, supra. G protein-coupled pheromone receptors in yeast control a developmental program that culminates in mating (fusion) of a and α haploid cell types to form the a/α diploid. See K. Blumer and J. Thorner, supra; I. Herskowitz, *Microbiol. Rev.* 52, 536 (1988).

The present invention is based on our continued research into the expression of heterologous G protein coupled receptors in yeast.

SUMMARY OF THE INVENTION

A first aspect of the present invention is a transformed yeast cell containing a first heterologous DNA sequence which codes for a mammalian G protein coupled receptor and a second heterologous DNA sequence which codes for a mammalian G protein α subunit (mammalian $G_\alpha$). The first and second heterologous DNA sequences are capable of expression in the cell, but the cell is incapable of expressing an endogenous G protein α-subunit (yeast $G_\alpha$). The cell optionally contains a third heterologous DNA sequence, with the third heterologous DNA sequence comprising a pheromone-responsive promotor and an indicator gene positioned downstream from the pheromone-responsive promoter and operatively associated therewith.

A second aspect of the present invention is a method of testing a compound for the ability to affect the rate of dissociation of $G_\alpha$ from $G_{\beta\tau}$ in a cell. The method comprises: providing a transformed yeast cell as described above; contacting the compound to the cell; and then detecting the rate of dissociation of $G_\alpha$ from $G_{\beta\tau}$ in the cell. The cells may be provided in an aqueous solution, and the contacting step carried out by adding the compound to the aqueous solution.

A third aspect of the present invention is a DNA expression vector capable of expressing a transmembrane protein into the cell membrane of yeast cells. The vector contains a first segment comprising at least a fragment of the extreme amino-terminal coding sequence of a yeast G protein coupled receptor. A second segment is positioned downstream from the first segment (and in correct reading frame therewith), with the second segment comprising a DNA sequence encoding a heterologous G protein coupled receptor.

A fourth aspect of the present invention is a yeast cell transformed by a vector as described above.

DETAILED DESCRIPTION OF THE INVENTION

Figure 1:
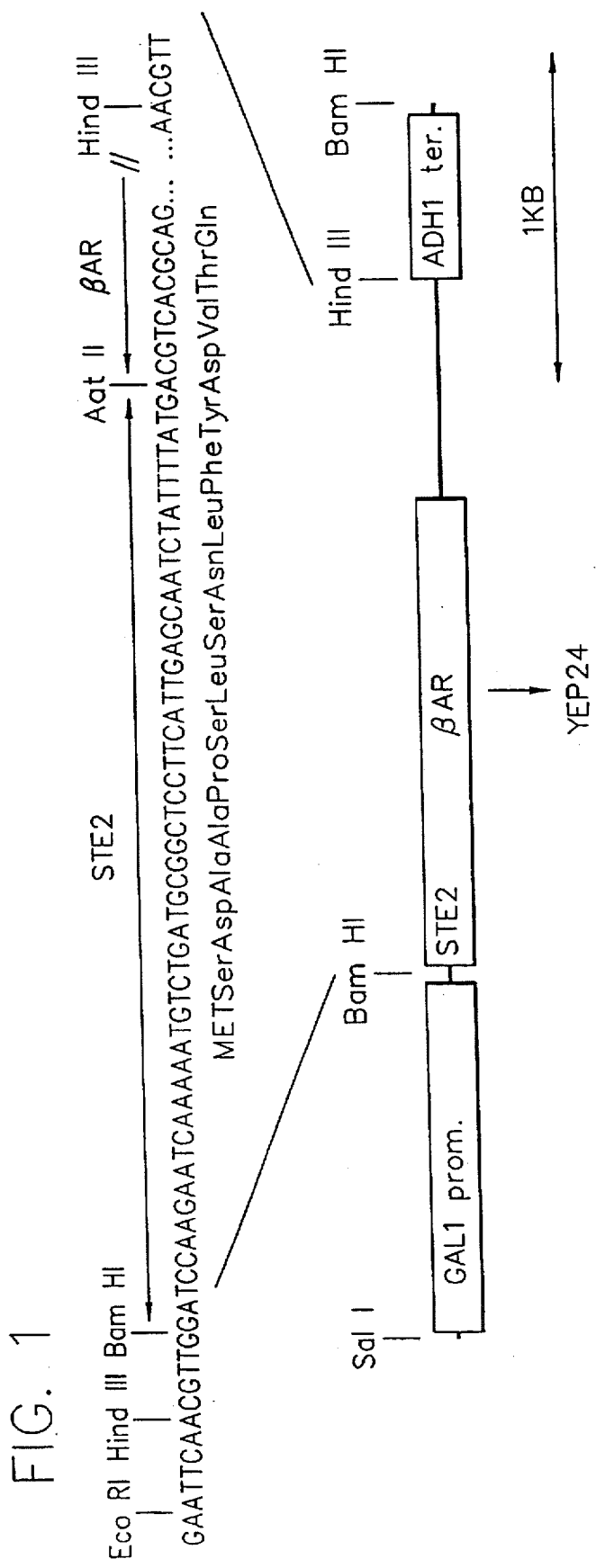
FIG. 1 illustrates the construction of the yeast human β2 Adrenergic Receptor expression plasmid, pYβAR2.

Nucleotide bases are abbreviated herein as follows:

| A = Adenine | G = Guanine |
|---|---|
| C = Cytosine | T = Thymine |

Amino acid residues are abbreviated herein to either three letters or a single letter as follows:

| Ala; A = Alanine | Leu; L = Leucine |
|---|---|
| Arg; R = Arginine | Lys; K = Lysine |
| Asn; N = Asparagine | Met; M = Methionine |
| Asp; D = Aspartic acid | Phe; F = Phenylalanine |
| Cys; C = Cysteine | Pro; P = Proline |
| Gln; Q = Glutamine | Ser; S = Serine |
| Glu; E = Glutamic acid | Thr; T = Threonine |
| Gly; G = Glycine | Trp; W = Tryptophan |
| His; H = Histidine | Tyr; Y = Tyrosine |
| Ile; I = Isoleucine | Val; V = Valine |

The term "mammalian" as used herein refers to any mammalian species (e.g., human, mouse, rat, and monkey).

The term "heterologous" is used herein with respect to yeast, and hence refers to DNA sequences, proteins, and other materials originating from organisms other than yeast (e.g., mammalian, avian, amphibian), or combinations thereof not naturally found in yeast.

The terms "upstream" and "downstream" are used herein to refer to the direction of transcription and translation, with a sequence being transcribed or translated prior to another sequence being referred to as "upstream" of the latter.

G proteins are comprised of three subunits: a guanyl-nucleotide binding α subunit; a β subunit; and a τ subunit. G proteins cycle between two forms, depending on whether GDP or GTP is bound thereto. When GDP is bound the $G_{\alpha\beta\tau}$ protein exists as an inactive heterotrimer, the $G_{\alpha\beta\tau}$ complex. When GTP is bound the α subunit dissociates, leaving a $G_{\beta\tau}$ complex. Importantly, when a $G_{\alpha\beta\tau}$ complex operatively associates with an activated G protein coupled receptor in a cell membrane, the rate of exchange of GTP for bound GDP is increased and, hence, the rate of dissociation of the bound the α subunit from the $G_{\beta\tau}$ complex increases. This fundamental scheme of events forms the basis for a multiplicity of different cell signaling phenomena. See generally Stryer and Bourne, supra.

Any mammalian G protein coupled receptor, and the DNA sequences encoding these receptors, may be employed in practicing the present invention. Examples of such receptors include, but are not limited to, dopamine receptors, muscarinic cholinergic receptors, α-adrenergic receptors, β-adrenergic receptors, opiate receptors, cannabinoid receptors, and serotonin receptors. The term receptor as used herein is intended to encompass subtypes of the named receptors, and mutants and homologs thereof, along with the DNA sequences encoding the same.

The human $D_1$ dopamine receptor cDNA is reported in A. Dearry et al., Nature 347, 72–76 (1990).

The rat $D_2$ dopamine receptor cDNA is reported in J. Bunzow et al., Nature 336, 783–787 (1988); see also O. Civelli, et al., PCT Appln. WO 90/05780 (all references cited herein are to be incorporated herein by reference).

Muscarinic cholinergic receptors (various subtypes) are disclosed in E. Peralta et al., Nature 343, 434 (1988) and K. Fukuda et al., Nature 327, 623 (1987).

Various subtypes of $\alpha_2$-adrenergic receptors are disclosed in J. Regan et al., Proc. Natl. Acad. Sci. USA 85, 6301 (1988) and in R. Lefkowitz and M. Caron, J. Biol. Chem. 263, 4993 (1988).

Serotonin receptors (various subtypes) are disclosed in S. Peroutka, Ann. Rev. Neurosci. 11, 45 (1988).

A cannabinoid receptor is disclosed in L. Matsuda et al., Nature 346, 561 (1990).

Any DNA sequence which codes for a mammalian G α subunit ($G_\alpha$) may be used to practice the present invention. Examples of mammalian G α subunits include $G_s$ α subunits, $G_i$ α subunits, $G_o$ α subunits, $G_z$ α subunits, and transducin α subunits. See generally Stryer and Bourne, supra. G proteins and subunits useful for practicing the present invention include subtypes, and mutants and homologs thereof, along with the DNA sequences encoding the same.

Heterologous DNA sequences are expressed in a host by means of an expression vector. An expression vector is a replicable DNA construct in which a DNA sequence encoding the heterologous DNA sequence is operably linked to suitable control sequences capable of effecting the expression of a protein or protein subunit coded for by the heterologous DNA sequence in the intended host. Generally, control sequences include a transcriptional promoter, an optional operator sequence to control transcription, a sequence encoding suitable mRNA ribosomal binding sites, and (optionally) sequences which control the termination of transcription and translation.

Vectors useful for practicing the present invention include plasmids, viruses (including phage), and integratable DNA fragments (i.e., fragments integratable into the host genome by homologous recombination). The vector may replicate and function independently of the host genome, as in the case of a plasmid, or may integrate into the genome itself, as in the case of an integratable DNA fragment. Suitable vectors will contain replicon and control sequences which are derived from species compatible with the intended expression host. For example, a promoter operable in a host cell is one which binds the RNA polymerase of that cell, and a ribosomal binding site operable in a host cell is one which binds the endogenous ribosomes of that cell.

DNA regions are operably associated when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Transformed host cells of the present invention are cells which have been transformed or transfected with the vectors constructed using recombinant DNA techniques and express the protein or protein subunit coded for by the heterologous DNA sequences. In general, the host cells are incapable of expressing an endogenous G protein α-subunit (yeast $G_\alpha$). The host cells do, however, express a complex of the G protein β subunit and the G protein τ subunit ($G_\alpha$). The host cells may express endogenous $G_{\beta\tau}$, or may optionally be engineered to express heterologous $G_{\beta\tau}$ (e.g., mammalian) in the same manner as they are engineered to express heterologous $G_\alpha$.

A variety of yeast cultures, and suitable expression vectors for transforming yeast cells, are known. See, e.g., U.S. Pat. No. 4,745,057; U.S. Pat. No. 4,797,359; U.S. Pat. No. 4,615,974; U.S. Pat. No. 4,880,734; U.S. Pat. No. 4,711,844; and U.S. Pat. No. 4,865,989. Saccharomyces cerevisiae is the most commonly used among the yeast, although a number of other strains are commonly available. See, e.g., U.S. Pat. No. 4,806,472 (Kluveromyces lactis and expression vectors therefor); U.S. Pat. No, 4,855,231 (Pichia pastoris and expression vectors therefor). Yeast vectors may contain an origin of replication from the 2 micron yeast plasmid or an autonomously replicating sequence (ARS), a promoter, DNA encoding the heterologous DNA sequences, sequences for polyadenylation and transcription termination, and a selection gene. An exemplary plasmid is YRp7, (Stinchcomb et al., Nature 282, 39 (1979); Kingsman et al., Gene 7, 141 (1979); Tschemper et al., Gene 10, 157 (1980)). This plasmid contains the trp1 gene, which provides a selection marker for a mutant strain of yeast lacking the ability to grow in tryptophan, for example ATCC No. 44076 or PEP4-1 (Jones, Genetics 85, 12 (1977)). The presence of the trp1 lesion in the yeast host cell genome then provides an effective environment for detecting transformation by growth in the absence of tryptophan.

Suitable promoting sequences in yeast vectors include the promoters for metallothionein, 3-phosphoglycerate kinase (Hitzeman et al., J. Biol. Chem. 255, 2073 (1980) or other glycolytic enzymes (Hess et al., J. Adv. Enzyme Reg. 7, 149 (1968); and Holland et al., Biochemistry 17, 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization.

In constructing suitable expression plasmids, the termination sequences associated with these genes may also be ligated into the expression vector 3' of the heterologous coding sequences to provide polyadenylation and termination of the mRNA.

A novel DNA expression vector described herein which is particularly useful for carrying out the present invention contains a first segment comprising at least a fragment of the extreme amino-terminal coding sequence of a yeast G protein coupled receptor and a second segment downstream from said first segment and in correct reading frame therewith, the second segment comprising a DNA sequence encoding a heterologous G protein coupled receptor (e.g., a mammalian G protein coupled receptor). In a preferred embodiment, this vector comprises a plasmid. In constructing such a vector, a fragment of the extreme amino-terminal coding sequence of the heterologous G protein coupled receptor may be deleted. The first and second segments are operatively associated with a promoter, such as the GAL1 promoter, which is operative in a yeast cell. Coding sequences for yeast G protein coupled receptors which may be used in constructing such vectors are exemplified by the gene sequences encoding yeast pheremone receptors (e.g., the STE2 gene, which encodes the α-factor receptor, and the STE3 gene, which encodes the a-factor receptor). The levels of expression obtained from these novel vectors are enhanced if at least a fragment of the 5'-untranslated region of a yeast G protein coupled receptor gene (e.g., a yeast pheromone receptor gene; see above) is positioned upstream from the first segment and operatively associated therewith.

Any of a variety of means for detecting the dissociation of $G_\alpha$ from $G_{\beta\tau}$ can be used in connection with the present invention. The cells could be disrupted and the proportion of these subunits and complexes determined physically (i.e., by chromatography). The cells could be disrupted and the quantity of $G_\alpha$ present assayed directly by assaying for the enzymatic activity possessed by $G_\alpha$ in isolation (i.e., the ability to hydrolyze GTP to GDP). Since whether GTP or GDP is bound to the G protein depends on whether the G protein exists as a $G_{\beta\tau}$ or $G_{\alpha\beta\tau}$ complex, dissociation can be probed with radiolabelled GTP. As explained below, morphological changes in the cells can be observed. A particularly convenient method, however, is to provide in the cell a third heterologous DNA sequence, wherein the third heterologous DNA sequence comprises a pheromone-responsive promotor and an indicator gene positioned downstream from the pheromone-responsive promoter and operatively associated therewith. This sequence can be inserted with a vector, as described in detail herein. With such a sequence in place, the detecting step can be carried out by monitoring the expression of the indicator gene in the cell. Any of a variety of pheromone responsive promoters could be used, examples being the BAR1 gene promoter and the FUS1 gene promoter. Likewise, any of a broad variety of indicator genes could be used, with examples including the HIS3 gene and the LacZ gene.

As noted above, transformed host cells of the present invention express the protein or protein subunit coded for by the heterologous DNA sequence. When expressed, the G protein coupled receptor is located in the host cell membrane (i.e., physically positioned therein in proper orientation for both the stereospecific binding of ligands on the extracellular side of the cell membrane and for functional interaction with G proteins on the cytoplasmic side of the cell membrane).

The ability to control the yeast pheromone response pathway by expression of a heterologous adrenergic receptor and its cognate G protein α-subunit has the potential to facilitate structural and functional characterization of mammalian G protein-coupled receptors. By scoring for responses such as growth arrest or β-galactosidase induction, the functional properties of mutant receptors can now be rapidly tested. Similarly, as additional genes for putative G protein-coupled receptors are isolated, numerous ligands can be screened to identify those with activity toward previously unidentified receptors. See F. Libert et al., *Science* 244, 569 (1989); M. S. Chee et al., *Nature* 344, 774 (1990). Moreover, as additional genes coding for putative G protein α-subunits are isolated, they can be expressed in cells of the present invention and screened with a variety of G protein coupled receptors and ligands to characterize these subunits. These cells can also be used to screen for compounds which affect receptor-G protein interactions.

Cells of the present invention can be deposited in the wells of microtiter plates in known, predetermined quantities to provide standardized kits useful for screening compounds in accordance with the various screening procedures described above.

The following Examples are provided to further illustrate various aspects of the present invention. They are not to be construed as limiting the invention.

EXAMPLE 1

Construction of the Human β2-Adrenergic Expression Vector pYβAR2 and Expression in Yeast To attain high level expression of the human β2-adrenergic receptor (hβAR) in yeast, a modified hβAR gene was placed under the control of the GAL1 promoter in the multicopy vector, YEp24 (pYβAR2).

FIG. 1 illustrates the construction of yeast expression plasmid pYβAR2. In pYβAR2, expression of the hβAR sequence is under the control of the GAL1 promoter. FIG. 1A shows the 5'-untranslated region and the first 63 base-pairs (bp) of coding sequence of the hβAR gene in pTZNAR. B. O'Dowd et al., *J. biol. Chem.* 263, 15985 (1988), which was removed by Aat II cleavage and replaced with a synthetic oligonucleotide corresponding to 11 bp of noncoding and 42 bp of coding sequence from the STE.2 gene. See N. Nakayama et al., *EMBO J.* 4, 2643 (1985); A. Burkholder and L. Hartwell, *Nucleic Acids Res.* 13, 8463 (1985). The resulting plasmid, pTZYNAR, contains the modified hβAR gene flanked by Hind III sites in noncoding sequences. The Hind III-Hind III fragment was isolated from pTZYNAR and inserted into pAAH5 such that the 3'-untranslated sequence of the modified hEAR gene was followed by 450 bp containing termination sequences from the yeast ADH1 gene. See G. Ammerer, *Methods. Enzymol.* 101, 192 (1983).

As illustrated in FIG. 1B, pyβ13AR2 was constructed by inserting the Bam HI—Bam HI fragment containing hβAR and ADJ1 sequences into YEpG24. E. Wyckoff and T. Hsieh, *Proc. Natl. Acad. Sci. U.S.A.* 85, 6272 (1988). Where maximum expression was sought, cells were cotransformed with plasmid pMTL9 (from Dr. S. Johnston) containing LAC9, a homolog of the *S. cerevisiae* GAL4 transactivator protein required for GAL1-regulated transcription. J. Salmeron et al., *Mol. Cell. Biol.* 9, 2950 (1989). Cells grown to late exponential phase were induced in medium containing 3% galactose, supplemented with about 10 μM alprenolol, and grown for an additional 36 hours. Standard methods for the maintenance of cells were used. See F. Sherman et al.,

*Methods in Yeast Genetics* (Cold Spring Harbor Laboratory, Cold Spring Harbor, N.Y., 1986).

Maximal expression required (i) expression of a transcriptional transactivator protein (LAC9), (ii) replacement of the 5' untranslated and extreme NH$_2$-terminal coding sequence of the hβAR gene with the corresponding region of the yeast STE2 (α-factor receptor) gene, (iii) induction with galactose when cell growth reached late exponential phase, and, (iv) inclusion of an adrenergic ligand in the growth medium during induction.

The plasmid pYβAR2 was deposited in accordance with the provisions of the Budapest Treaty at the American Type Culture Collection, 12301 Parklawn Drive, Rockville, Md. 20852 USA, on Sep. 11, 1990, and has been assigned ATCC Accession No. 40891.

EXAMPLE 2

Binding Affinity of hβAR Ligands in Yeast Transformed with pYβAR2

A primary function of cell surface receptors is to recognize only appropriate ligands among other extracellular stimuli. Accordingly, ligand binding affinities were determined to establish the functional integrity of hβAR expressed in yeast. As discussed in detail below, an antagonist, $^{125}$-labeled cyanopindolol ($^{125}$I-CYP), bound in a saturable manner and with high affinity to membranes prepared from pYβAR2-transformed yeast cells. By displacement of $^{125}$I-CYP with a series of agonists, the order of potency and stereospecificity expected for hβAR was observed.

SC261 cells (MATa ura3-52 trp1 leu2 prb1-1122 pep4-3 prc1-407) (from Dr. S. Johnston) harboring pYβAR2 (URA3) and pMTL9 (LEU2) were grown in minimal glucose-free selective media to late log phase (OD$_{600}$=5.0), and then induced with the addition of 3% galactose and 40 μM alprenolol. After 36 hours, cells were harvested and spheroplasts were prepared as described. See E. Wyckoff and T. Hsieh, *Proc. Natl. Acad. Sci. U.S.A.* 85, 6272 (1988). Briefly, the spheroplasts were resuspended in 50 mM Tris-HCl pH 7.4, 5 mM EDTA and were lysed by vortex mixing with glass beads for three one-min periods at 4° C. Crude membranes were prepared from the lysates and binding assays with $^{125}$I-CYP were performed by methods described previously. See H. Dohlman et al., *Biochemistry* 29, 2335 (1990).

Figure 2A:
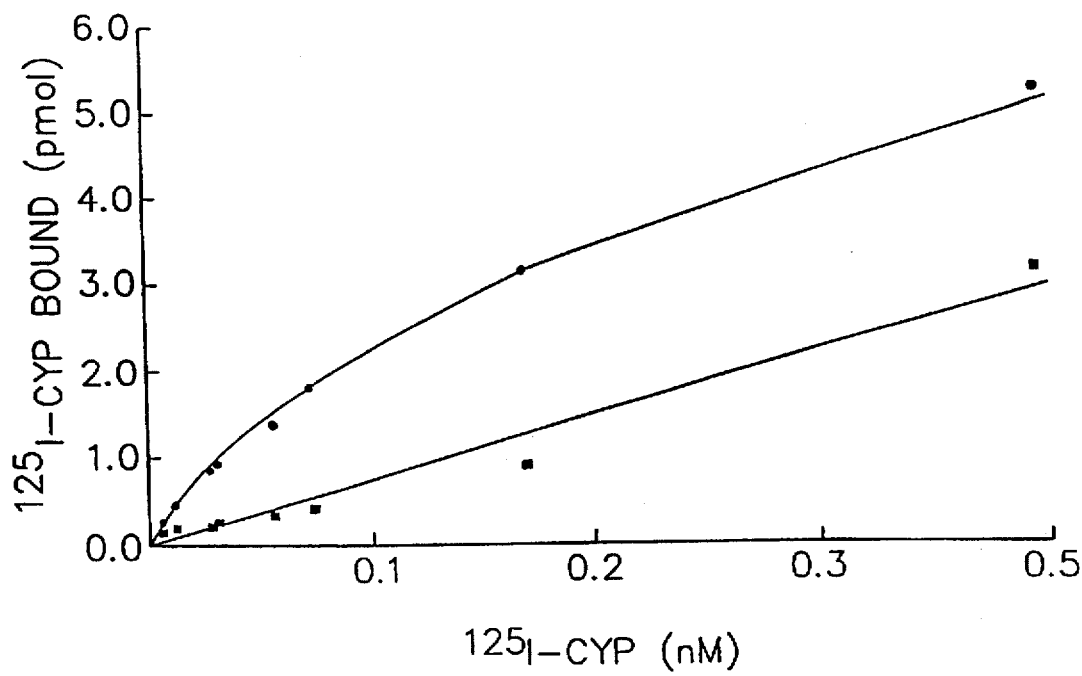
FIG. 2 illustrates hβAR ligand binding to membranes from pYβAR2-transformed yeast cells.
Figure 2B:
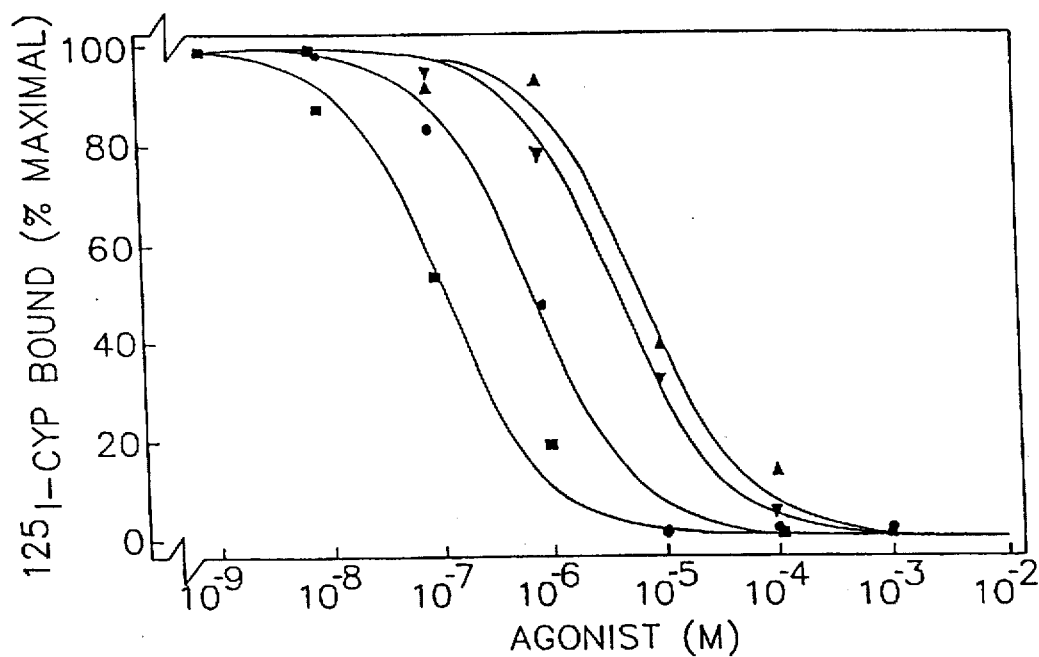

FIG. 2 illustrates hβAR ligand binding to membranes from pYβAR2-transformed yeast cells. (A) B$_{max}$ (maximum ligand bound) and K$_d$ (ligand dissociation constant) values were determined by varying 125$_I$-CYP concentrations (5–400 pM). Specific binding was defined as the amount of total binding (circles) minus nonspecific binding measured in the presence of 10 μM (−) alprenolol (squares). A K$_d$ of 93 pM for 125$_I$-CYP binding was obtained and used to calculate agonist affinities (below). (B) Displacement of 18 pM 125$_I$-CYP with various concentrations of agonists was used to determine apparent low affinity K$_i$ values (non G protein coupled, determined in the presence of 50 μM GTP) for receptor binding, squares; (−) isoproterenol, circles; (−) epinephrine, downward-pointing triangles; (+) isoproterenol, upward pointing triangles; (−) norepinephrine.

COMPARATIVE EXAMPLE A

Ligand Binding Affinity for hβAR Expressed in Yeast and Mammalian Cells

The binding data of FIGS. 2(A) and (B) were analyzed by nonlinear least squares regression, see A. DeLean et al., *Mol. Pharmacol.* 21, (1982), and are presented in Table I. Values given are averages of measurements in triplicate, and are representative of 2 −3 experiments. Binding affinities in yeast were nearly identical to those observed previously for hβAR expressed in mammalian cells.

TABLE 1

Comparison of ligand Binding Parameters for High Level Expression of Human β-Adrenergic Receptor in Yeast and COS-7 Cells*

|  | Yeast SC261 (pY, βAR2, pMTL9) | Monkey COS-7 (pBC12:β,BAR) |
|---|---|---|
| 125$_I$-CYP: | | |
| $^1$K$_d$ | 0.093 nM ± 0.013 | 0.110 nM ± 0.009 |
| $^2$B$_{max}$ | 115 pmol/mg | 24 pmol/mg |
| $^3$K$_i$ (M): | | |
| (−) isoproterenol | 103 ± 26 | 130 ± 15 |
| (+) isoproterenol | 3670 ± 420 | 4000 ± 184 |
| (−) epinephrine | 664 ± 123 | 360 ± 30 |
| (−) norepinephrine | 6000 ± 1383 | 5800 ± 373 |

*Values derived from FIG. 2 and H. Dohlman et al., Biochemistry 29, 2335 (1990).; ± S.E.
$^1$K$_d$, ligand dissociation constant
$^2$B$_{max}$, maximum ligand bound
$^3$K$_i$, inhibition constant

EXAMPLE 3

Agonist-Dependent Activation of Mating Signal Transduction in Yeast Expressing hβAR A second major function of a receptor is agonist-dependent regulation of downstream components in the signal transduction pathway. Because the pheromone-responsive effector in yeast is not known, indirect biological assays are the most useful indicators of receptor functionality. See K. Blumer and J. Thorner, *Annu. Rev. Physiol.* in press; I. Herskowitz, *Microbiol. Rev.* 52, 536 (1988). In yeast cells expressing high concentrations of hβAR, no agonist-dependent activation of the mating signal transduction pathway could be detected by any of the typical in vivo assays; for example, imposition of G1 arrest, induction of gene expression, alteration of morphology (so-called "shmoo" formation) or stimulation of mating. A likely explanation for the absence of responsiveness is that hβAR was unable to couple with the endogenous yeast G protein.

EXAMPLE 4

Coexpression of hβAR and Mammalian G, α-Subunit in Yeast

Expression of a mammalian G$_s$ α-subunit can correct the growth defect in yeast cells lacking the corresponding endogenous protein encoded by the GPA1 gene. See C. Dietzel and J. Kurjan, *Cell* 50, 1001 (1987). Moreover, specificity of receptor coupling in mammalian cells is conferred by the α-subunit of G proteins. See L. Stryer and H. Bourne, *Annu. Rev. Cell Biol.* 2, 391 (1988). Thus, coexpression of hβAR and a mammalian G$_s$ α-subunit (GSα) in yeast was attempted to render the yeast responsive to adrenergic ligands. Accordingly, a cDNA encoding rat G$_s$α under the control of the copper-inducible CUP1 promoter was introduced on a second plasmid, pYSK136Gαs. See C. Dietzel and J. Kurjan, *Cell* 50, 1001 (1987). In yeast (NNY19) coexpressing hβAR and rat G$_s$α, but containing wild-type GPA1, no adrenergic agonist-induced shmoo formation, a characteristic morphological change of yeast in response to mating pheromone, was observed.

EXAMPLE 5

Coexpression of hβAR and Mammalian G_sα-Subunit in Yeast Lacking an Endogenous G Protein α-Subunit To prevent interference by the endogenous yeast G protein α-subunit, gpa1 mutant cells (strain 8c) were used.

Yeast strain 8c (MATa ura3 leu2 his3 trp1 gpa1::H153), I. Miyajima et al., Cell 59, 1011 (1987), carrying plasmids pYSK136Gαs (TRP1), C. Dietzel and J. Kurjan, Cell 50, 1001 (1987), pMTL9 (LEU2), J. Salmeron et al., Mol. Cell. Biol. 9, 2950 (1989), and pYβAR2 (URA3) was maintained on glucose-free minimal selective plates containing 3% glycerol, 2% lactic acid, 50 μM CuSO$_4$ and 3% galactose. Colonies were transferred to similar plates containing 0.5 mM ascorbic acid and the indicated adrenergic ligand(s). After 16–20 hours at 30° C., the colonies were transferred to similar liquid media at a density of $10^6$–$10^7$ cells/ml and examined by phase contrast microscopy.

Morphologies of yeast cells cotransformed with pYβAR2, pMTL9, and pYSK136Gαs were examined after incubation with (A) no adrenergic agent; (B) 100 μM (–) isoproterenol; (C) 100 μM (–) isoproterenol and 50 μM (–) alprenolol; and (D) 100 μM (+) isoproterenol. Results showed that treatment of 8c cells coexpressing hβAR and rat G_sα with the β-adrenergic agonist isoproterenol indeed induced shmoo formation, and that this effect was blocked by the specific antagonist alprenolol.

EXAMPLE 6

Coexpression of hβAR and Mammalian G_sα-Subunit in Yeast Containing a β-Galactosidase Signal Sequence The isoproterenol-induced morphological response of 8c cells coexpressing hβAR and rat G_sα suggested that these components can couple to each other and to downstream components of the pheromone response pathway in yeast lacking the endogenous G α-subunit. To confirm that the pheromone signaling pathway was activated by hβAR and rat G_sα, agonist induction of the pheromone-responsive FUS1 gene promoter was measured in a strain of yeast derived from 8c cells (8cI) in which a FUS1-lacZ gene fusion had been stably integrated into the genome. See S. Nomoto et al., EMBO J. 9, 691 (1990).

Strains 8c (FIG. 3, legend) and NNY19 (MATa ura3 leu2 his3 trp1 lys2 FUS1-LacZ::LEU2) were modified by integrative transformation with YIpFUS102 (LEU2), S. Nomoto et al., supra, and designated 8cI and NNY19, respectively. These strains were transformed with pYβAR2 and pYSK136Gαs and maintained on minimal selective plates containing glucose and 50 μM CuSO$_4$. Colonies were inoculated into minimal selective media (3% glycerol, 2% lactic acid, 50 μM CuSO$_4$), grown to early log phase (OD$_{600}$=1.0), and induced for 12 hours by addition of 3% galactose. Cells were washed and resuspended in induction media (OD$_{600}$= 5.0) containing 0.5 mM ascorbic acid and the indicated ligands. After a 4 hour incubation at 30° C., cells were harvested, resuspended into 1 ml of Z-buffer, see J. Miller, Experiments in Molecular Genetics (Cold Spring Harbor Laboratory, Cold Spring Harbor, N.Y., 1972), supplemented with 0.0075% SDS, and β-galactosidase activities were determined in 3–4 independent experiments as described previously. See J. Miller, supra.

Figure 3:
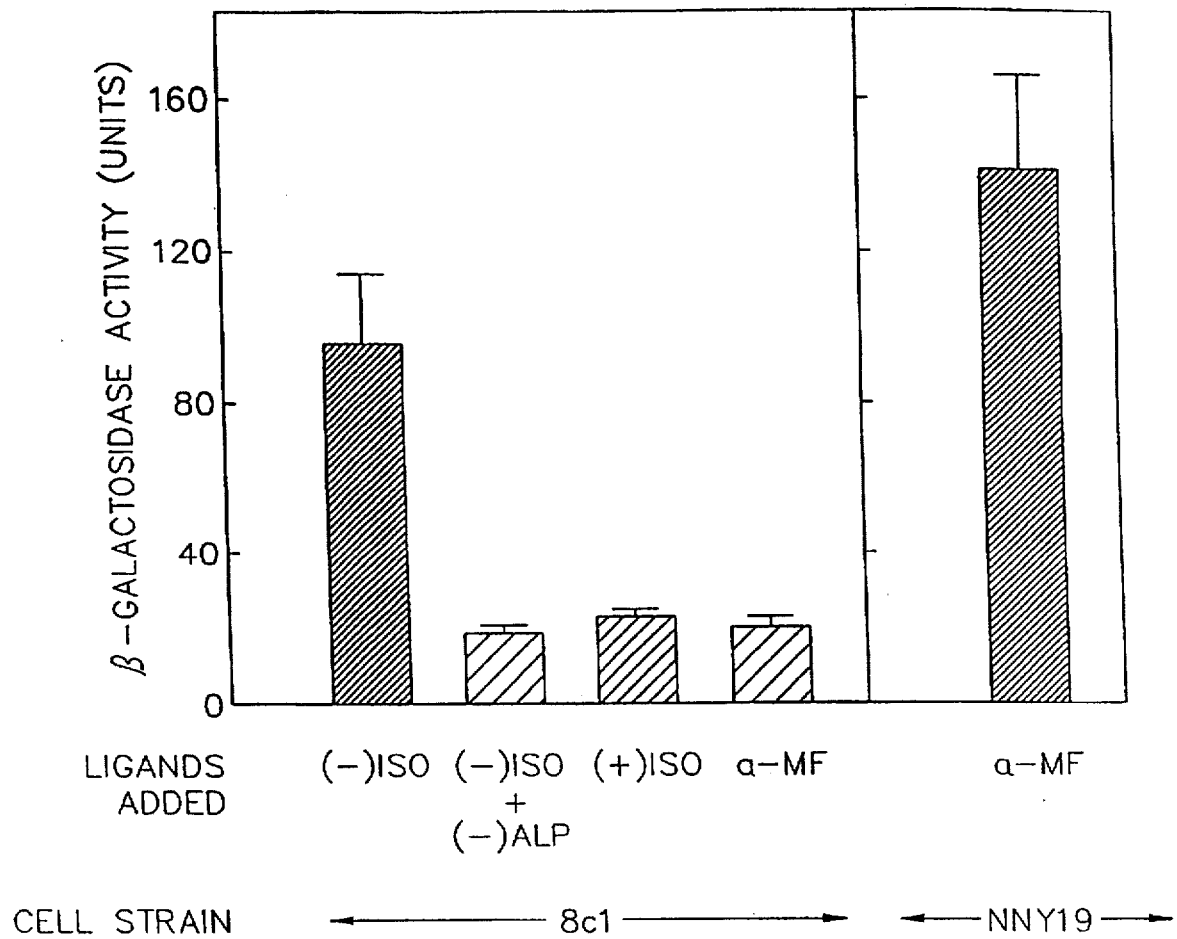
FIG. 3 shows a comparison of β-adrenergic agonist effects on pheromone-inducible gene activity. α-MF, 10 μM α-mating factor; (−) ISO, 50 μM (−) isoproterenol; (−) ALP, 50 μM (−) alprenolol; (+) ISO, 100 μM (+) isoproterenol.

FIG. 3 shows a comparison of β-adrenergic agonist effects on pheromone-inducible gene activity. α-MF, 10 μM α-mating factor; (–) ISO, 50 μM (–) isoproterenol; (–) ALP, 50 μM (–) alprenolol; (+) ISO, 100 μM (+) isoproterenol. In 8cI (gpa1) cells coexpressing hβAR and rat G_sα, a dramatic isoproterenol-stimulated induction of β-galactosidase activity was observed. Agonist stimulation was stereoselective and was blocked by addition of a specific antagonist. Agonist responsiveness was dependent on expression of both hβAR and rat G_sα, and required a strain in which the endogenous G protein α-subunit was disrupted. The final β-galactosidase activity achieved in response to isoproterenol in transformed 8cI cells was comparable to that induced by α-factor in nontransformed cells that express GPA1 (NNY19), although basal β-galactosidase activity in NNY19 cells was considerably lower than in 8cI cells. Taken together, our results indicated that coexpression of hβAR and rat G_sα was sufficient to place under catecholamine control key aspects of the mating signal transduction pathway in yeast. However, the adrenergic agonist did not stimulate mating in either 8c cells or NNY19 cells coexpressing hβAR and rat G_sα, in agreement with recent observations that yeast pheromone receptors, in addition to binding pheromones, participate in other recognition events required for mating. See A. Bender and G. Sprague, Genetics 121, 463 (1989).

hβAR stimulates adenylate cyclase in animal cells via the action of the α-subunit of its G protein. In contrast, mating factor receptors in yeast trigger their effector via the action of the βγ subunits. M. Whiteway et al., Cell 56, 476 (1989). Our present results indicate that activation of hβAR in yeast leads to dissociation of mammalian G_sα from yeast βγ, and it is the βγ subunits that presumably elicit the response.

The foregoing examples are illustrative of the present invention, and are not to be construed as limiting thereof. The invention is defined by the following claims, with equivalents of the claims to be included therein.

That which is claimed is:

1. A DNA expression vector capable of expressing a transmembrane protein into the cell membrane of a yeast cell, said yeast cell lacking an endogenous G protein α subunit and expressing a mammalian Gs α subunit, said vector comprising:

a first segment encoding at least the first 14 contiguous amino acids from the extreme amino-terminal sequence of a yeast G protein coupled receptor; and a second segment downstream from said first segment and in correct reading frame therewith, said second segment comprising a DNA sequence encoding a heterologous G protein coupled receptor, wherein said heterologous receptor couples to said mammalian Gs α subunit and transduces a pheromone responsive signal in said yeast cell; and wherein, agonist binding to said heterologous G protein coupled receptor in said yeast cell is sufficient to activate detectable expression of a reporter gene operatively linked to a pheromone responsive promoter.

2. A DNA expression vector according to claim 1, wherein said yeast G protein coupled receptor is selected from the group consisting of the STE2 gene product and the STE3 gene product.

3. A DNA expression vector according to claim 1 or 2, wherein said first and second segments are operatively associated with a promoter operative in a yeast cell.

4. A DNA expression vector according to claim 3, wherein said promoter is the GAL1 promoter.

5. A DNA expression vector according to claim 1 or 2, further comprising a 5'-untranslated regulatory region of a yeast G protein coupled receptor gene positioned upstream from said first segment and operatively associated therewith.

6. A DNA expression vector according to claim 1 or 2, further comprising a 5'-untranslated regulatory region of a yeast pheromone receptor gene positioned upstream from said first segment and operatively associated therewith.

7. A DNA expression vector according to claim 6, wherein said yeast pheromone receptor gene is selected from the group consisting of the STE2 gene and the STE3 gene.

8. A DNA expression vector according to claim 1 or 2, said vector comprising a plasmid.

9. A DNA expression vector according to claim 1 or 2, said second segment comprising a DNA sequence encoding a mammalian G protein-coupled receptor selected from the group consisting of dopamine receptors.

10. A yeast cell carrying a DNA expression vector according to claim 1 or 2.

11. The yeast cell of claim 10, further comprising a heterologous DNA sequence including an indicator gene which is operatively associated with a pheromone responsive promoter.

12. The yeast cell of claim 11, wherein the pheromone responsive promoter is selected from the group consisting of a BAR1 gene promoter and a Fus1 gene promoter.

* * * * *

UNITED STATES PATENT AND TRADEMARK OFFICE
CERTIFICATE OF CORRECTION

PATENT NO. : 5,739,029
DATED : April 14, 1998
INVENTOR(S) : Klim King, et al.

It is certified that error appears in the above-identified patent and that said Letters Patent is hereby corrected as shown below:

ON THE TITLE PAGE:

In the Abstract, line 10, please replace "$G\beta\tau$" with --$G\beta\gamma$--.

Column 1, line 63, please replace "$G\beta\tau$" with --$G\beta\gamma$--.

Column 1, line 66, please replace "$G\beta\tau$" with --$G\beta\gamma$--.

Column 2, line 61, please replace "$\tau$" with --$\gamma$--.

Column 2, line 63, please replace "$G\beta\alpha\tau$" with --$G\beta\alpha\gamma$--.

Column 2, line 64, please replace "$G\beta\alpha\tau$" with --$G\beta\alpha\gamma$--.

Column 2, line 65, please replace "$G\beta\tau$" with --$G\beta\gamma$--.

Column 2, line 66, please replace "$G\beta\alpha\tau$" with --$G\beta\alpha\gamma$--.

Column 3, line 4, please replace "$G\beta\tau$" with --$G\beta\gamma$--.

Column 4, line 19, please replace "$\tau$" with --$\gamma$--.

Column 4, line 20, please replace "$G\beta\tau$" with --$G\beta\gamma$--.

Column 4, line 21, please replace "$G\beta\tau$" with --$G\beta\gamma$--.

UNITED STATES PATENT AND TRADEMARK OFFICE
CERTIFICATE OF CORRECTION

PATENT NO. : 5,739,029
DATED : April 14, 1998
INVENTOR(S) : Klim King, et al.

It is certified that error appears in the above-identified patent and that said Letters Patent is hereby corrected as shown below:

Column 5, line 32, please replace "G$\beta\tau$" with --G$\beta\gamma$--.

Column 5, line 40, please replace "G$\beta\tau$ or G$\alpha\beta\tau$" with --G$\beta\gamma$ or G$\beta\alpha\gamma$--.

Column 10, line 32, please replace "$\beta\tau$" with --$\beta\gamma$--.

Column 10, line 34, please replace "$\beta\tau$" with --$\beta\gamma$--.

Column 10, line 35, please replace "$\beta\tau$" with --$\beta\gamma$--.

Column 12, line 4. after "dopamine receptors," please add

--$\alpha$-adrenergic receptors, and $\beta$-adrenergic receptors--.

Signed and Sealed this

Twenty-second Day of February, 2000

Attest:

*Attesting Officer*

Q. TODD DICKINSON
*Commissioner of Patents and Trademarks*